(12) United States Patent
Tanaka et al.

(10) Patent No.: US 10,814,499 B2
(45) Date of Patent: Oct. 27, 2020

(54) ACTUATOR DEVICE AND CONTROL METHOD

(71) Applicant: KAWASAKI JUKOGYO KABUSHIKI KAISHA, Kobe-shi, Hyogo (JP)

(72) Inventors: Hideki Tanaka, Nishinomiya (JP); Hideki Watanabe, Kobe (JP); Mariko Ogata, Kobe (JP); Isamu Yoshimura, Kobe (JP); Tomohide Hattori, Miki (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 0 days.

(21) Appl. No.: 16/099,903

(22) PCT Filed: May 9, 2017

(86) PCT No.: PCT/JP2017/017575
§ 371 (c)(1),
(2) Date: Nov. 8, 2018

(87) PCT Pub. No.: WO2017/195786
PCT Pub. Date: Nov. 16, 2017

(65) Prior Publication Data
US 2019/0143540 A1    May 16, 2019

(30) Foreign Application Priority Data

May 11, 2016   (JP) .................................. 2016-095509

(51) Int. Cl.
*A61B 17/00*   (2006.01)
*B25J 19/00*   (2006.01)
(Continued)

(52) U.S. Cl.
CPC ............... *B25J 19/00* (2013.01); *A61B 17/00* (2013.01); *B25J 9/144* (2013.01); *B25J 13/088* (2013.01);
(Continued)

(58) Field of Classification Search
CPC .................. F15B 7/001; A61B 2017/00539
See application file for complete search history.

(56) References Cited

U.S. PATENT DOCUMENTS 5,791,231 A * 8/1998 Cohn ....................... B25J 9/144
606/1
2004/0182231 A1   9/2004 Yo et al.
2005/0200195 A1   9/2005 Yogo

FOREIGN PATENT DOCUMENTS

JP   H11-270503 A    10/1999
JP   2001214903 A *   8/2001
(Continued)

*Primary Examiner* — F Daniel Lopez
(74) *Attorney, Agent, or Firm* — Oliff PLC

(57) ABSTRACT

A piston accommodated in an internal space of a cylinder and forming a pair of pressure chambers together with the cylinder, the piston being configured to move relative to the cylinder; a first actuator connected to one pair of pressure chambers; a second actuator connected to the other of the pair of pressure chambers; a position detector configured to detect a position of the piston relative to the cylinder; a pressure detector configured to detect a pressure of one pair of pressure chambers; and a controller configured to control the first actuator and the second actuator. The controller controls one of the first actuator and the second actuator that the position detected by the position detector is made close to a target position and controls the other of the first actuator and the second actuator that the pressure detected by the pressure detector is made close to a target pressure.

4 Claims, 1 Drawing Sheet

(51) Int. Cl.
  *B25J 9/14*   (2006.01)
  *F15B 7/00*   (2006.01)
  *B25J 13/08*  (2006.01)
  *F15B 21/08*  (2006.01)
  *F15B 7/10*   (2006.01)
  *F15B 9/02*   (2006.01)
  *F15B 11/028* (2006.01)

(52) U.S. Cl.
  CPC ................ F15B 7/001 (2013.01); F15B 7/10 (2013.01); F15B 9/02 (2013.01); F15B 11/028 (2013.01); F15B 21/087 (2013.01); *A61B 2017/00539* (2013.01); *F15B 2211/20515* (2013.01); *F15B 2211/633* (2013.01); *F15B 2211/6313* (2013.01); *F15B 2211/6336* (2013.01); *F15B 2211/6651* (2013.01); *F15B 2211/6653* (2013.01); *F15B 2211/6656* (2013.01); *F15B 2211/7053* (2013.01); *F15B 2211/75* (2013.01); *F15B 2211/76* (2013.01); *F15B 2211/7656* (2013.01)

(56) References Cited

FOREIGN PATENT DOCUMENTS

| | | |
|---|---|---|
| JP | 2004-263645 A | 9/2004 |
| JP | 2004-286122 A | 10/2004 |
| JP | 2008-298226 A | 12/2008 |
| JP | 2015-100677 A | 6/2015 |

\* cited by examiner

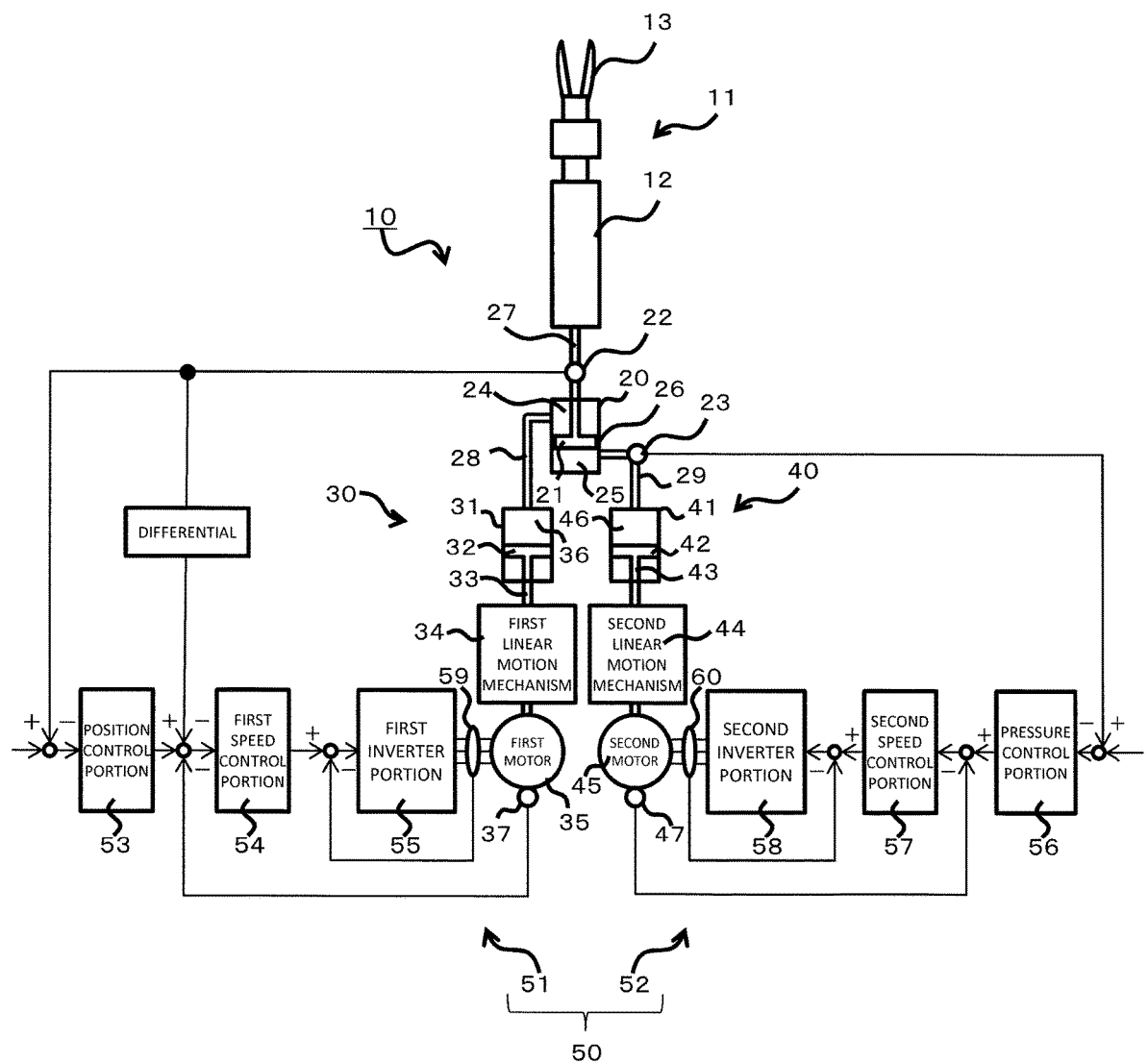

ACTUATOR DEVICE AND CONTROL METHOD

TECHNICAL FIELD

The present invention relates to an actuator device including a cylinder and a control method.

BACKGROUND ART

A surgical robot of PTL 1 is known as one example using an actuator device including a cylinder. The surgical robot includes a forceps, and a piston and a cylinder are provided at the forceps so as to open and close an opening/closing portion of the forceps.

Further, for example, a hydraulic device of PTL 2 is known as a device configured to control a pressure of a pressure chamber of the cylinder while positioning the piston. The hydraulic device includes a hydraulic cylinder, a rod, a hydraulic pump connected to the hydraulic cylinder through a channel, and an electric motor configured to drive the hydraulic pump. The electric motor is controlled based on a position of the rod relative to the hydraulic cylinder and a pressure in the channel connected to the cylinder. Then, such position control and pressure control are switched from one to the other.

CITATION LIST

Patent Literature

PTL 1: Japanese Laid-Open Patent Application Publication No. 2015-100677
PTL 2: Japanese Laid-Open Patent Application Publication No. 2004-263645

SUMMARY OF INVENTION

Technical Problem

Since the cylinder of the surgical robot of PTL 1 is small, frictional force between the piston and the cylinder is large relative to thrust acting on the piston. Therefore, when the piston is moved relative to the cylinder, a stick-slip phenomenon easily occurs by a difference between kinetic friction resistance and static friction resistance which act between the cylinder and the piston. With this, the piston does not move smoothly, and highly-accurate positioning cannot be performed.

In order to improve positioning accuracy, the pressure of the pressure chamber of the cylinder is required to be kept constant. However, according to the hydraulic device of PTL 2, since the position control and the pressure control are performed while being switched from one to the other, it is difficult to keep the pressure of the cylinder constant. Therefore, highly-accurate positioning cannot be maintained.

The present invention was made to solve the above problems, and an object of the present invention is to provide an actuator device and a control method, each of which is capable of performing positioning with a high degree of accuracy.

Solution to Problem

An actuator device according to one aspect of the present invention includes: a cylinder including an internal space; a piston accommodated in the internal space and forming a pair of pressure chambers together with the cylinder, the piston being configured to move relative to the cylinder; a first actuator connected to one of the pair of pressure chambers; a second actuator connected to the other of the pair of pressure chambers; a position detector configured to detect a position of the piston relative to the cylinder; a pressure detector configured to detect a pressure of any one of the pair of pressure chambers; and a controller configured to control the first actuator and the second actuator, wherein: the controller controls one of the first actuator and the second actuator such that the position detected by the position detector is made close to a target position; and the controller controls the other of the first actuator and the second actuator such that the pressure detected by the pressure detector is made close to a target pressure.

According to this configuration, the position of the piston relative to the cylinder can be controlled by one of the first actuator and the second actuator, and at the same time, the pressure in the cylinder partitioned by the piston can be controlled by the other of the first actuator and the second actuator. Therefore, the piston can be positioned with a high degree of accuracy, and the positioning accuracy can be kept high In this actuator device, the cylinder may be a hydraulic cylinder configured such that pressures of liquids of the pair of pressure chambers are controlled by the respective first and second actuators or a pneumatic cylinder configured such that pressures of gases of the pair of pressure chambers are controlled by the respective first and second actuators.

In the actuator device, each of the first actuator and the second actuator may be a hydraulic cylinder or a pneumatic cylinder.

The actuator device may further include a rod including: a tip end connected to a treating part of a medical instrument; and a base end coupled to the piston. With this, the treating part of the medical instrument which requires high positioning accuracy can be linked with the movement of the piston, and thus, can be positioned with a high degree of accuracy.

A method of controlling an actuator device according to another aspect of the present invention is a method of controlling an actuator device, the actuator device including: a cylinder including an internal space; a piston accommodated in the internal space and forming a pair of pressure chambers together with the cylinder, the piston being configured to move relative to the cylinder; a first actuator connected to one of the pair of pressure chambers; a second actuator connected to the other of the pair of pressure chambers; a position detector configured to detect a position of the piston relative to the cylinder; and a pressure detector configured to detect a pressure of any one of the pair of pressure chambers, the method including: controlling one of the first actuator and the second actuator such that the position detected by the position detector is made close to a target position; and controlling the other of the first actuator and the second actuator such that the pressure detected by the pressure detector is made close to a target pressure.

Advantageous Effects of Invention

The present invention is configured as explained above and has an effect of being able to provide an actuator device and a control method, each of which is capable of performing positioning with a high degree of accuracy.

The above object, other objects, features, and advantages of the present invention will be made clear by the following detailed explanation of preferred embodiments with reference to the attached drawings.

BRIEF DESCRIPTION OF DRAWINGS

FIG. 1 is a block diagram schematically showing the configuration of an actuator device according to an embodiment of the present invention.

DESCRIPTION OF EMBODIMENTS

Hereinafter, embodiments of the present invention will be specifically explained with reference to the drawings. In the following explanations and the drawings, the same reference signs are used for the same or corresponding components, and a repetition of the same explanation is avoided.

Embodiment

First, the configuration of an actuator device 10 according to an embodiment of the present invention will be explained with reference to FIG. 1. The following will explain a case where the actuator device 10 according to the present invention is applied to a medical instrument 11. However, the present embodiment is not limited to the case where the actuator device 10 is applied to the medical instrument 11.

For example, the medical instrument 11 is connected to a manipulator (not shown) of a robot arm. Examples of the medical instrument 11 include a forceps, a cautery, an electric scalpel, and an image pickup apparatus. In the present embodiment, the forceps is adopted. The medical instrument 11 includes the actuator device 10, a movable portion 12, and a treating part 13. An opening/closing portion of the forceps is used as the treating part 13. The movable portion 12 is a link mechanism and converts movements of the actuator device 10 into movements corresponding to the treating part 13. In the present embodiment, the movable portion 12 converts movements of a piston 21 into opening/closing operations of the opening/closing portion that is the treating part 13.

The actuator device 10 includes a cylinder 20, the piston 21, a first actuator 30, a second actuator 40, a position detector 22, a pressure detector 23, and a controller 50. For example, the controller 50 may be connected to an input device (not shown) to which a command is input by manipulation of a user.

The cylinder 20 is a hydraulic cylinder. A liquid, such as oil or a physiological saline solution, is used as an operating fluid. The cylinder 20 is a small cylinder having a small diameter, and the diameter is about 5 mm, for example. The cylinder 20 includes an internal space and is constituted by, for example, a cylindrical side wall portion and end wall portions covering both respective end openings of the side wall portion. The piston 21 is accommodated in the internal space of the cylinder 20.

The piston 21 has, for example, a disc shape and forms a pair of pressure chambers 24 and 25 together with the cylinder 20. A packing 26 is provided at a side end of the piston 21. The packing 26 is made of resin, rubber, and the like and is interposed in a gap between the side end of the piston 21 and the side wall portion of the cylinder 20. With this, the packing 26 seals the gap while realizing a state where the piston 21 can move relative to the cylinder 20.

A rod 27 is, for example, a rod-shaped long member, and a base end of the rod 27 is coupled to the piston 21. The rod 27 passes through the internal space of the cylinder 20 and penetrates the end wall portion of the cylinder 20. The treating part 13 of the medical instrument 11 is connected to a tip end of the rod 27.

The first actuator 30 is connected to the pressure chamber 24 (in the present embodiment, a rod-side pressure chamber) that is one of the pair of pressure chambers 24 and 25 through a first passage 28. The rod-side pressure chamber 24 is a rod 27-side pressure chamber through which the rod 27 passes. The first actuator 30 supplies or discharges a liquid to or from the rod-side pressure chamber 24 through the first passage 28 to adjust a pressure of the liquid in the rod-side pressure chamber 24.

In the present embodiment, the first actuator 30 is a hydraulic cylinder. The first actuator 30 includes a first cylinder 31, a first piston 32, a first rod 33, a first linear motion mechanism 34, and a first motor 35. The first cylinder 31 is a hydraulic cylinder. A head-side pressure chamber (head-side first pressure chamber) 36 of the first cylinder 31 communicates with the rod-side pressure chamber 24 of the cylinder 20 through the first passage 28. The first rod 33 extends from the first piston 32 and is connected to the first motor 35 through the first linear motion mechanism 34. The first motor 35 is, for example, a servo motor that can rotate in both directions. A rotational movement of the first motor 35 is controlled by the controller 50. A first rotating speed sensor 37 configured to detect a rotating speed of the first motor 35 is provided at the first motor 35, and a detected position detected by the first rotating speed sensor 37 is output to the controller 50. The first linear motion mechanism 34 converts the rotational movement of the first motor 35 into a straight movement, and the straight movement is transmitted to the first piston 32 through the first rod 33.

The second actuator 40 is connected to the pressure chamber 25 (in the present embodiment, a head-side pressure chamber) that is the other of the pair of pressure chambers 24 and 25 through a second passage 29. The head-side pressure chamber 25 is a head-side pressure chamber through which the rod 27 does not pass. The second actuator 40 supplies or discharges the liquid to or from the head-side pressure chamber 25 through the second passage 29 to adjust the pressure of the liquid in the head-side pressure chamber 25.

In the present embodiment, the second actuator 40 is a hydraulic cylinder. The second actuator 40 includes a second cylinder 41, a second piston 42, a second rod 43, a second linear motion mechanism 44, and a second motor 45. The second cylinder 41 is a hydraulic cylinder. A head-side pressure chamber (head-side second pressure chamber) 46 of the second cylinder 41 communicates with the head-side pressure chamber 25 of the cylinder 20 through the second passage 29. The second rod 43 extends from the second piston 42 and is connected to the second motor 45 through the second linear motion mechanism 44. The second motor 45 is, for example, a servo motor that can rotate in both directions. A rotational movement of the second motor 45 is controlled by the controller 50. A second rotating speed sensor 47 configured to detect a rotating speed of the second motor 45 is provided at the second motor 45, and a detected position detected by the second rotating speed sensor 47 is output to the controller 50. The second linear motion mechanism 44 converts the rotational movement of the second motor 45 into a straight movement, and the straight movement is transmitted to the second piston 42 through the second rod 43.

The position detector 22 is a sensor configured to detect a position of the piston 21 relative to the cylinder 20. One example of the position detector 22 is a sensor utilizing light or magnetism. The position of the piston 21 is a position in a moving direction of the piston 21, for example, a position in a direction perpendicular to the piston 21 having the disc shape. Further, for example, the position of the piston 21 may be: a value obtained by integrating movement distances from an initial value; or a distance from a reference position of the cylinder 20 to the piston 21. For example, the position detector 22 is provided at the rod 27 and outputs the detected position to the controller 50.

The pressure detector 23 is a sensor configured to detect the pressure of the head-side pressure chamber 25 of the cylinder 20 and outputs the detected pressure to the controller 50. Examples of the pressure detector 23 include a strain gage and a sensor utilizing a piezoelectric effect. In the present embodiment, the pressure detector 23 is provided at the second passage 29. However, the pressure detector 23 may be provided at the head-side pressure chamber 25 or the head-side second pressure chamber 46 of the second cylinder 41.

The controller 50 includes a calculating portion (not shown) and a storage portion (not shown). The controller 50 is, for example, a robot controller including a computer, such as a microcontroller. It should be noted that the controller 50 may be constituted by a single controller which performs centralized control or a plurality of controllers which cooperate to perform distributed control.

Used as the storage portion is a ROM, a RAM, and the like, and the storage portion stores information, such as a basic program for the robot controller and various fixed data. Used as the calculating portion is a CPU or the like. The calculating portion reads and executes software, such as the basic program stored in the storage portion, to control the first and second actuators 30 and 40 of the actuator device 10.

The controller 50 includes a first control portion 51 and a second control portion 52. The first control portion 51 includes a position control portion 53, a first speed control portion 54, and a first inverter portion 55. The second control portion 52 includes a pressure control portion 56, a second speed control portion 57, and a second inverter portion 58. The first inverter portion 55 is connected to the first motor 35 through a first wire, and a first current sensor 59 is provided at the first wire. The second inverter portion 58 is connected to the second motor 45 through a second wire, and a second current sensor 60 is provided at the second wire.

For example, the first control portion 51 controls one of the first actuator 30 and the second actuator 40 (in the present embodiment, the first actuator 30) such that the position detected by the position detector 22 is made close to a target position. The second control portion 52 controls the other of the first actuator 30 and the second actuator 40 (in the present embodiment, the second actuator 40) such that the pressure detected by the pressure detector 23 is made close to a target pressure.

Next, an operation (control method) of the actuator device 10 will be explained with reference to FIG. 1. This operation is controlled by the controller 50. For example, by manipulation of the input device by the user, the target position is input to the first control portion 51, and the target pressure is input to the second control portion 52.

The target position is such a position of the piston 21 that the medical instrument 11 is arranged at an arrival position. The target pressure may be a pressure that changes depending on various conditions or may be a constant pressure that does not change. For example, the target pressure is such a pressure that the position of the piston 21 can be maintained so as not to be changed when external force is applied to the medical instrument 11 or when the direction of the medical instrument changes, and this changes the gravity of the medical instrument 11 acting on the piston 21. Further, the target pressure is such a pressure that the frictional force between the cylinder 20 and the piston 21 is made as small as possible relative to the thrust of the piston 21 in order to suppress a stick-slip phenomenon when the piston 21 moves. At this time, the target pressure is set in consideration of the durability of the cylinder 20 and the like.

The position control portion 53 of the first control portion 51 acquires the position (current position) of the piston 21 from the position detected by the position detector 22. Then, the position control portion 53 calculates a difference (positional difference) between the target position of the piston 21 and the current position of the piston 21 and calculates a target rotating speed of the first motor 35, the target rotating speed corresponding to the positional difference. For example, when the positional difference is large, the target rotating speed of the first motor 35 is set to be high in order to increase the rotating speed of the first motor 35. When the positional difference is zero, the target rotating speed of the first motor 35 is set to zero. With this, the rotating speed of the first motor 35 becomes zero, and the piston 21 is positioned at the target position.

The first speed control portion 54 acquires the rotating speed (current rotating speed) of the first motor 35 detected by the first rotating speed sensor 37. Then, the first speed control portion 54 calculates a difference (speed difference) between the current rotating speed of the first motor 35 and the target rotating speed of the first motor 35 and calculates a target current corresponding to the speed difference. It should be noted that a relation between the speed difference and the target current is determined in advance.

The first inverter portion 55 acquires the current (detected current) detected by the first current sensor 59 and calculates a difference (current difference) between the target current and the detected current. Then, the first inverter portion 55 controls the rotation of the first motor 35 such that the current difference is made small.

With this, the first motor 35 rotates, and this rotational movement is transmitted to the first piston 32 through the first linear motion mechanism 34. The first piston 32 moves relative to the first cylinder 31 in accordance with the positional difference. When the first piston 32 moves to the head side, the liquid is supplied from the head-side first pressure chamber 36 to the rod-side pressure chamber 24.

In contrast, when the first piston 32 moves toward the first rod 33, the liquid is discharged from the rod-side pressure chamber 24 to the head-side first pressure chamber 36. By the thrust corresponding to a differential pressure between the rod-side pressure chamber 24 and the head-side pressure chamber 25 by the supply or discharge of the liquid, the first piston 32 moves to the target position, and the medical instrument 11 connected to the first piston 32 is arranged at the arrival position.

On the other hand, the pressure control portion 56 of the second control portion 52 acquires the pressure (current pressure) of the rod-side pressure chamber 24 of the cylinder 20 from the pressure detected by the pressure detector 23. Then, the pressure control portion 56 calculates a difference (pressure difference) between the target pressure of the rod-side pressure chamber 24 and the current pressure of the rod-side pressure chamber 24 and calculates the target rotating speed of the second motor 45 in accordance with the pressure difference. A relation between the pressure difference and the target rotating speed of the second motor 45 is determined in advance. For example, as the pressure difference increases, the target rotating speed of the second motor 45 is set to increase in order to increase the rotating speed of the second motor 45. When the pressure difference is zero, the target rotating speed of the second motor 45 is set to zero. With this, the rotating speed of the second motor 45 becomes zero, and the pressure of the rod-side pressure chamber 24 is kept at the target pressure.

The second speed control portion 57 acquires the rotating speed (current rotating speed) of the second motor 45 detected by the second rotating speed sensor 47. Then, the second speed control portion 57 calculates a difference (speed difference) between the current rotating speed of the second motor 45 and the target rotating speed of the second motor 45 and calculates the target current corresponding to the speed difference. It should be noted that a relation between the speed difference and the target current is determined in advance.

The second inverter portion 58 acquires the current (detected current) detected by the second current sensor 60, calculates a difference (current difference) between the target current and the detected current, and controls the rotation of the second motor 45 such that the current difference is made small.

With this, the second motor 45 rotates, and this rotational movement is transmitted to the second piston 42 through the second linear motion mechanism 44. The second piston 42 moves relative to the second cylinder 41 in accordance with the pressure difference. With this, when the second piston 42 moves to the head side, the liquid is supplied from the head-side second pressure chamber 46 to the head-side pressure chamber 25. In contrast, when the second piston 42 moves toward the second rod 43, the liquid is discharged from the head-side pressure chamber 25 to the head-side second pressure chamber 46. By the supply or discharge of the liquid, the pressure of the head-side pressure chamber 25 is adjusted to the target pressure.

As above, the cylinder 20 is controlled by the first actuator 30 and the second actuator 40. With this, two variables that are the position of the piston 21 relative to the cylinder 20 and the pressure of the pressure chamber of the cylinder 20 can be controlled at the same time.

The position of the piston 21 relative to the cylinder 20 is controlled by one of the first actuator 30 and the second actuator 40, and the pressure of the pressure chamber of the cylinder 20 is controlled by the other of the first actuator 30 and the second actuator 40. With this, while moving the piston 21 to the target position, the pressure of the pressure chamber of the cylinder 20 can be adjusted to an arbitrary optimal pressure corresponding to various conditions.

Thrust F of the piston 21 is determined based on force F1 applied from the liquid of the rod-side pressure chamber 24, force F2 applied from the liquid of the head-side pressure chamber 25, and other force F3. The force F1 of the rod-side pressure chamber 24 is calculated by a product of the pressure acting on the piston 21 from the liquid of the rod-side pressure chamber 24 and the area of the piston 21 on which the liquid of the rod-side pressure chamber 24 acts. The force F2 of the head-side pressure chamber 25 is calculated by a product of the pressure acting on the piston 21 from the liquid of the head-side pressure chamber 25 and the area of the piston 21 on which the liquid of the head-side pressure chamber 25 acts. One example of the other force F3 is the frictional force between the piston 21 and the cylinder 20.

The thrust F of the piston 21 is represented by "$F=|F1-F2|-F3$." When F1 and F2 are extremely larger than F and F3 ($F, F3 \ll F1, F2$), the position of the piston 21 can be determined with a high degree of accuracy.

When the pressure of the rod-side pressure chamber 24 is adjusted such that the frictional force between the cylinder 20 and the piston 21 becomes small relative to the thrust of the piston 21, the stick-slip phenomenon can be suppressed, and the piston 21 can be positioned with a high degree of accuracy.

Other Embodiments

In the above embodiment, a hydraulic cylinder is used as the cylinder 20. Instead, a pneumatic cylinder may be used as the cylinder 20. In this case, air or the like is used as an operating fluid in the pneumatic cylinder.

In the above embodiment, the first actuator 30 includes the first cylinder 31 and the like, and the second actuator 40 includes the second cylinder 41 and the like. However, the above embodiment is not limited to this as long as the first actuator 30 can adjust the pressure of the liquid of the rod-side pressure chamber 24 of the cylinder 20, and the second actuator 40 can adjust the pressure of the liquid of the head-side pressure chamber 25 of the cylinder 20.

In the above embodiment, hydraulic cylinders are used as the first cylinder 31 and the second cylinder 41. Instead, a pneumatic cylinder may be used as one or each of the first cylinder 31 and the second cylinder 41. In this case, air or the like is used as the operating fluid in the pneumatic cylinder.

In the above embodiment, the first actuator 30 is connected to the rod-side pressure chamber 24 of the cylinder 20, and the second actuator 40 is connected to the head-side pressure chamber 25 of the cylinder 20. However, the above embodiment is not limited to this. The first actuator 30 may be connected to the head-side pressure chamber 25 of the cylinder 20, and the second actuator 40 may be connected to the rod-side pressure chamber 24 of the cylinder 20.

In the above embodiment, the position of the piston 21 relative to the cylinder 20 is controlled by the first actuator 30, and the pressure of the head-side pressure chamber 25 of the cylinder 20 is controlled by the second actuator 40. However, the above embodiment is not limited to this. The position of the piston 21 relative to the cylinder 20 may be controlled by the second actuator 40, and the pressure of the head-side pressure chamber 25 of the cylinder 20 may be controlled by the first actuator 30. Further, the position control and the pressure control may be switched from one to the other during control. In this case, the pressure detector 23 is provided at the first passage 28, the rod-side pressure chamber 24, or the head-side first pressure chamber 36 and detects the pressure of the rod-side pressure chamber 24 of the cylinder 20.

In the above embodiment, the target current of the first motor 35 is calculated from the current rotating speed of the first motor 35, the current rotating speed being based on the detected value detected by the first rotating speed sensor 37. However, the above embodiment is not limited to this. The target current of the first motor 35 may be calculated from the movement speed of the piston 21.

In this case, for example, the first speed control portion 54 acquires the movement speed (current movement speed) of the piston 21, the movement speed being obtained by differentiating the detected position detected by the position detector 22. Then, the first speed control portion 54 calculates a difference (speed difference) between the current movement speed and the target rotating speed supplied from the position control portion 53 and calculates the target current corresponding to the speed difference. A relation between the speed difference and the target current is determined in advance.

In the above embodiment, the second control portion 52 includes the pressure control portion 56, the second speed control portion 57, and the second inverter portion 58. Then, the pressure control portion 56 calculates the target rotating speed of the second motor 45 in accordance with the pressure difference, and the second speed control portion 57 calculates the target current in accordance with the difference between the target rotating speed and the current rotating speed supplied from the second rotating speed sensor 47. Instead, the second control portion 52 may include the pressure control portion 56 and the second inverter portion 58. In this case, the pressure control portion 56 may calculate the target current of the second motor 45 in accordance with the pressure difference. It should be noted that a relation between the pressure difference and the target current is determined in advance.

In the above embodiment, the actuator device 10 may further include a correcting portion, and the correcting portion may be included in the controller 50. For example, when the target position and the target pressure are input from the input device, the correcting portion may correct the target position in accordance with conditions, such as a current position, a load condition, an individual difference, and ambient surroundings. With this, the piston 21 can be positioned at the target position with a higher degree of accuracy in accordance with the conditions.

In the above embodiment, the pressure detector 23 detects the pressure of the head-side pressure chamber 25 of the cylinder 20. However, the pressure detector 23 may detect the pressure of the rod-side pressure chamber 24 of the cylinder 20. In this case, the pressure detector 23 may be provided at the first passage 28, the rod-side pressure chamber 24, or the head-side first pressure chamber 36.

In the above embodiment, the first rotating speed sensor 37 is provided at the first motor 35, and the second rotating speed sensor 47 is provided at the second motor 45. However, a first position sensor may be provided at the first motor 35 instead of the first rotating speed sensor 37, and a second position sensor may be provided at the second motor 45 instead of the second rotating speed sensor 47. In this case, the first position sensor detects the position of a rotor of the first motor 35, stores a rotation amount of the first motor 35, and outputs the rotation amount to the controller 50. The second position sensor detects the position of a rotor of the second motor 45, stores a rotation amount of the second motor 45, and outputs the rotation amount to the controller 50. The first speed control portion 54 of the controller 50 calculates the rotating speed (current rotating speed) of the first motor 35 by differentiating the rotation amount of the first position sensor, and the second speed control portion 57 of the controller 50 calculates the rotating speed (current rotating speed) of the second motor 45 by differentiating the rotation amount of the second position sensor.

The above embodiments may be combined with one another as long as they do not exclude each other.

From the foregoing explanation, many modifications and other embodiments of the present invention are obvious to one skilled in the art. Therefore, the foregoing explanation should be interpreted only as an example and is provided for the purpose of teaching the best mode for carrying out the present invention to one skilled in the art. The structures and/or functional details may be substantially modified within the scope of the present invention.

INDUSTRIAL APPLICABILITY

The actuator device and the control method according to the present invention are useful as, for example, an actuator device and a control method, each of which can perform positioning with a high degree of accuracy.

REFERENCE SIGNS LIST 10 actuator device
12 medical instrument
20 cylinder
21 piston
22 position detector
23 pressure detector
24 rod-side pressure chamber (pressure chamber)
25 head-side pressure chamber (pressure chamber)
27 rod
30 first actuator
40 second actuator
50 controller

The invention claimed is:

1. An actuator device comprising:
a cylinder including an internal space;
a piston accommodated in the internal space and forming a pair of pressure chambers together with the cylinder, the piston being configured to move relative to the cylinder;
a first actuator connected to one of the pair of pressure chambers and including a first fluid cylinder, a first electric motor, and a first linear motion mechanism;
a second actuator connected to the other of the pair of pressure chambers and including a second fluid cylinder, a second electric motor, and a second linear motion mechanism;
a position detector configured to detect a position of the piston relative to the cylinder;
a pressure detector configured to detect a pressure of any one of the pair of pressure chambers; and
a controller configured to control the first actuator and the second actuator, wherein:
the controller controls the first actuator such that the position detected by the position detector is made close to a target position;
the controller controls the second actuator such that the pressure detected by the pressure detector is made close to a target pressure;
when controlling the first actuator, the controller calculates a target rotating speed of the first electric motor based on the target position and the position of the piston detected by the position detector; and
the controller controls rotation of the first electric motor based on the target rotating speed and a current movement speed of the piston corresponding to the position of the piston detected by the position detector.

2. The actuator device according to claim 1, wherein the cylinder is (i) a hydraulic cylinder configured such that pressures of liquids of the pair of pressure chambers are controlled by the respective first and second actuators or (ii) a cylinder configured such that pressures of gases of the pair of pressure chambers are controlled by the respective first and second actuators.

3. The actuator device according to claim 1, further comprising a rod including: a tip end connected to a treating part of a medical instrument; and a base end coupled to the piston.

4. A method of controlling an actuator device, the actuator device comprising:

a cylinder including an internal space;

a piston accommodated in the internal space and forming a pair of pressure chambers together with the cylinder, the piston being configured to move relative to the cylinder;

a first actuator connected to one of the pair of pressure chambers and including a first fluid cylinder, a first electric motor, and a first linear motion mechanism;

a second actuator connected to the other of the pair of pressure chambers and including a second fluid cylinder, a second electric motor, and a second linear motion mechanism;

a position detector configured to detect a position of the piston relative to the cylinder; and a pressure detector configured to detect a pressure of any one of the pair of pressure chambers, the method comprising:

controlling the first actuator such that the position detected by the position detector is made close to a target position;

controlling the second actuator such that the pressure detected by the pressure detector is made close to a target pressure;

when controlling the first actuator, calculating a target rotating speed of the first electric motor based on the target position and the position of the piston detected by the position detector; and controlling rotation of the first electric motor based on the target rotating speed and a current movement speed of the piston corresponding to the position of the piston detected by the position detector.

* * * * *